United States Patent [19]
Wagner et al.

[11] Patent Number: 5,858,361
[45] Date of Patent: Jan. 12, 1999

[54] MONOCLONAL ANTI-IDIOTYPIC ANTI-CA125 ANTIBODIES AND PHARMACEUTICAL COMPOSITIONS CONTAINING THEM

[76] Inventors: Uwe Wagner, Troschelstrasse 5; Harald Schlebusch, Blücherstrasse 21, both of 53115 Bonn, Germany

[21] Appl. No.: 553,407
[22] PCT Filed: May 26, 1994
[86] PCT No.: PCT/EP94/01719
§ 371 Date: Feb. 26, 1996
§ 102(e) Date: Feb. 26, 1996
[87] PCT Pub. No.: WO94/27637
PCT Pub. Date: Dec. 8, 1994

[30] Foreign Application Priority Data

May 27, 1993 [EP] European Pat. Off. ............ 93 108 583

[51] Int. Cl.[6] ........................ A61K 39/395; C07K 16/00; C12N 16/86; C12N 15/00
[52] U.S. Cl. ..................... 424/131.1; 530/388.1; 530/388.25; 435/69.6; 435/327; 435/337; 435/346; 424/141.1
[58] Field of Search ............................. 424/141.1, 131.1, 424/138.1; 530/388.1, 388.25; 435/240.27, 69.6, 337, 327, 346

[56] References Cited

PUBLICATIONS

Ransberg et al, Clin. Chem. 36/1, 164–167 (1990) Evidence for Interaction of Human Anti Id Antibodies with CA125 Determination in a Patent after Radioimmunodetection.

Ray Chaudline et al J Immunol 139:271–278, 1987 (Jul. 1).

Morrison Science vol. 229, pp. 1202–1206 (1985).

Sandhu, Critical Reviews in Biotechnology vol. 12/5,6 1992 pp. 440–443.

*Primary Examiner*—Lila Feisee
*Assistant Examiner*—Geetha P. Bansal
*Attorney, Agent, or Firm*—John P. White; Cooper & Dunham LLP

[57] ABSTRACT

Disclosed is an anti-idiotypic antibody which reacts with an anti-CA125 antibody and competes with CA125 in its binding to said anti-idiotypic antibody are disclosed which have essentially the same binding specificity. Additionally, the invention relates to cell lines, particularly to hybridoma 3D5 (DSM ACC2120), producing said anti-idiotypic antibodies. Also disclosed are pharmaceutical compositions containing said anti-idiotypic antibodies and specific uses of these antibodies.

27 Claims, 8 Drawing Sheets

MONOCLONAL ANTI-IDIOTYPIC ANTI-CA125 ANTIBODIES AND PHARMACEUTICAL COMPOSITIONS CONTAINING THEM

The present invention relates to monoclonal anti-idiotypic antibodies reacting with anti-CA125 antibodies and competing with CA125 in binding to said anti-CA125 antibodies.

Furthermore, the invention relates to hybridomas producing said monoclonal anti-idiotypic antibodies. The present invention also relates to a method for the production of said monoclonal anti-CA125 antibodies and to pharmaceutical compositions containing them. These pharmaceutical compositions are useful for the treatment of CA125-positive malignant tumors, particularly epithelial ovarian cancer.

Up to now, the positive effect of an immunotherapy using tumor-associated antigens or tumor cells of ovarian carcinomas is still unproved. Although many unique tumor-associated antigens have been described and were used for vaccinations, a tumor rejection could only be seen occasionally and the failure of the immune system to destroy tumor cells is not clearly understood; Raychaudhuri et al., J. Immunology 139 (1987), 271. One of the reasons might be that different classes of available tumor-associated antigens (TAA) fail to induce an effective anti-tumor response; Dalgleish and Kennedy, Vaccine 6 (1988), 215, and Lee et al., Proc. Natl. Acad. Sci. USA 82 (1985), 6286. The most common TAAs belong to the class III tumor-associated antigens and are found on both malignant and a number of normal cells, but they are usually expressed at a higher concentration on the malignant cells.

Therefore, an explanation for the absence of an anti-tumor immunity in patients might be the close relationship of the tumor-associated antigens (class III) and self-antigens and that the host's immune system has been tolerized by the tumor antigen by slowly increasing antigen doses. Furthermore, a patient suffering from a carcinoma is mostly immunosuppressed; Wagner et al., Tumordiagnostik & Therapie 11 (1990), 1.

An effective way to overcome an experimentally induced tolerance is to present the relevant antigen in a different molecular environment to the tolerized immune system, but this can only be done for well-defined and easily purifyable antigens: Raychaudhuri et al., J. Immunology 137 (1986), 1743. According to the network hypothesis of Niels Jerne, the immune system consists of antibodies and lymphocytes which interact through complementary structures; Jerne, Ann. Immunol. (Paris) 125C (1974), 373. The interlymphocytic connections depend on the variable region structures presented on antibody molecules or specific receptors. In this system, "internal image" antibodies express a special idiotype mimicking the original antigenic epitope, which can thus be presented to the immune system by the variable region of such antibody molecules. Such antibodies are defined as anti-idiotypic antibodies-beta (=Ab2β), if they bear the internal image of a distinct antigen; Cerny and Hiernaux, "Concept of Idiotypic Network: Description and Functions in Idiotypic Network and Diseases", Cerny and Hiernaux, Eds., American Society for Microbiology, Washington, 1990; Raychaudhuri et al., J. Immunology, 139 (1987), 271.

The alternative approach to overcome immunological tolerance is to initiate the idiotypic network using antibodies (named Ab1) against a tumor-associated antigen. This induces the production of anti-idiotypic antibodies (Ab2β) mimicking the "internal image" of the tumor-associated antigen. The principle is to transform the critical epitope of the TAA into an idiotypic determinant expressing the mirror image of the tumor-associated antigen on the surface of the antigen binding region of an antibody; Cerny and Hiernaux, supra. The Ab1 may induce Ab2, which are then capable of inducing $Id^+$ ($Ab1^+$) B-cells or $Id^+$ $T_H$ cells or cause a suppression of the proposed anti-tumor reaction by the induction of $Id^+T_S$ cells; Cerny and Hiernaux, supra, Raychaudhuri et al., J. Immunology, 137 (1987), 2096, Wettendorff et al., Proc. Natl. Acad. Sci. USA 86 (1989), 3787.

In summary, the Ab2β is able to induce a specific anti-tumor immunity in two ways. First, the Ab2β can present the critical epitope in a different way and as a consequence, modulate the immune system of the patient. Second, the Ab2β can induce the production of an Ab3, which by itself binds the tumor antigen (see FIG. 1); Cerny and Hiernaux, supra. The new "Antigen Mimicry" concept says that all idiotypes are regulatory and predicts that both external antigens and idiotypes trigger the same regulatory interactions to produce a specific response; Cerny and Hiernaux, supra.

Ovarian cancer is clearly the most frequent cause of death of all gynaecologic cancers. The cancer of the ovary has an incidence of 15 new cancer patients among 100.000 women every year. The survival rates and, thus, the prognosis of patients with this type of cancer are very poor; Gloeckler-Ries, Cancer 71 (1993), 524, Schmidt-Matthiesen and Bastert: "Gynäkologische Onkologie", Schattauer, New York, 1987, Zander, ed.: "Ovarialkarzinom—Fortschritte für das diagnostische und therapeutische Handeln", Urban & Schwarzenberg, Munich, 1982. About 80% of these cancers will only be detected in advanced stages and 60% of all ovarian cancer patients suffer from tumor masses larger than 10 cm at the time of operation. However, ovarian carcinomas also seem to be tumors which are often rapidly proliferating and the survival rate of chemotherapy-resistant tumors will be about 6 months; Gloeckler-Ries, supra, Schmidt-Matthiesen and Bastert, supra, Zander, supra. The overall 5-year-survival-rate for all stages is between 20 and 30%. For the extended stages of disease (III to IV), including extension of the disease in the whole abdominal cavity and/or lymphnode metastasis (IIIa-c) or metastasis in other organs, such a lung and intrahepatical liver metastasis (VI), the survival rate is only about 10%, Schmidt-Matthiesen, supra.

A high-molecular mass glycoprotein called CA125 was detected in 80% of all ovarian carcinomas. As this glycoprotein is expressed on tumor tissue, the secretion of this molecule into the patient's plasma could be correlated to the tumor burden. The surveillance of the concentration of CA125 provides a tool for the observation of the clinical state and, also, information about remission or progression of the disease; Schmidt-Matthiesen and Basters, supra. Such molecules were defined as "Tumor Marker" and the glycoprotein by itself is a so-called "Tumor-Associated Antigen" (TAA). Tumor-associated antigens, which are also expressed on normal tissues of the organism, but at lower amounts, are defined as tumor-associated antigens class III. The CA125 tumor-associated antigen was also detected on normal tissues of the organs in the pelvis, like uterus and endometrium, fallopian tube, the ovaries and the serosa of the abdominal and thoracal cavity.

Murine monoclonal antibodies against this tumor-associated antigen were developed in 1981 and 1988; Bast et al., J. clin. Invest. 68 (1981), 1331, Krantz et al., J. Cell Biochem. (Suppl.)12 E(1988), 139. These antibodies were used for the determination of CA125 concentrations in in vitro assays and, furthermore, they were used as radiolabeled antibodies in humans in order to perform radioimmunodetection by localizing the distributed radiolabeled antibodies by scintigraphy in the tumor-bearing patient as a matter of diagnosis and posttherapeutical surveillance.

In spite of the development of radical surgical techniques and polychemotherapeutical treatment regimes, the overall prognosis of this cancer is not satisfactorily improved. Thus, it will be necessary to develop new techniques of treatment modalities; Zander, supra. Therefore, there remains the need in the art for effective treatments of ovarian carcinomas based on techniques that overcome the negative effects of known concepts such as radical surgical techniques and polychemotherapeutical treatments.

Thus, the technical problem underlying the present invention is to provide new compounds for the treatment of malignancies which are characterized by displaying a CA125 tumor-associated antigen to provide pharmaceutical compositions containing said compounds and to provide methods for producing said compounds.

The solution to said technical problem is achieved by providing the embodiments characterized in the claims.

Accordingly, the present invention relates to anti-idiotypic antibodies which react with an anti-CA125 antibody and compete with the CA125 antigen in its binding to said anti-CA125 antibody. It is believed that such anti-idiotypic antibodies are capable of inducing an immunoresponse to the CA125 tumor-associated antigen, i.e., of inducing a specific anti-tumor immunity.

In this context, the term "competes" means that said anti-idiotypic antibody has an affinity to the anti-CA125 antibody which is at least the same as that of CA125 due to the possession of an epitope which corresponds to an epitope of CA125.

The present invention is based on the following clinical observations. The effect of the induction of anti-idiotypic antibodies against the tumor-associated antigen on the survival rate of patients suffering from ovarian carcinoma at advanced stages was evaluated during the first studies of the inventors. Thus, patient were exposed to F(ab)$_2$-fragments of the mAb-OC125 against the TAA CA125 for several times in order to induce a human IgG anti-mAb-OC125 response; Reinsberg et al., Clin. Chem. 36 (1990), 164). These survival rates were compared to a similar group of patients without the induction of the network system, but being treated with the same surgical and chemotherapeutical therapy mode; Wagner et al., supra.

28 patients with advanced ovarian carcinomas (Stage II-IV FIGO) received 131-I-labeled-F(ab)$_2$-fragments of the OC125mAb (IMA-CIS-2) (International CIS, GIF-SUR-YVETTE, France) against the tumor-associated antigen CA125 in case of radioimmunodetection for diagnostic purposes (RID) (1 mg, intravenously) between the years 1985 and 1990; Wagner et al., Biotechnology Therapeutics 3 (1992), 81.

The antibody was administered more than three times to 9 of the patients. All of these patients developed high plasma levels of an anti-idiotypic antibody (Ab2β) against the OC125-fragments mimicking the tumor-associated antigen CA125; Reinsberg et al., supra.

The activation of the idiotypic network was performed for patients suffering from ovarian adenocarcinomas with preoperative high plasma values of the TAA CA125 accompanying the usual therapy procedures consisting of radical tumor-reduction and polychemotherapy.

The highest response in the induction of anti-idiotypic antibodies was detected after the following application schedule. The first RID was performed after three cycles of polychemotherapy after radical surgery, the second one after six weeks and a boostering administration after another three months.

Figure 2:
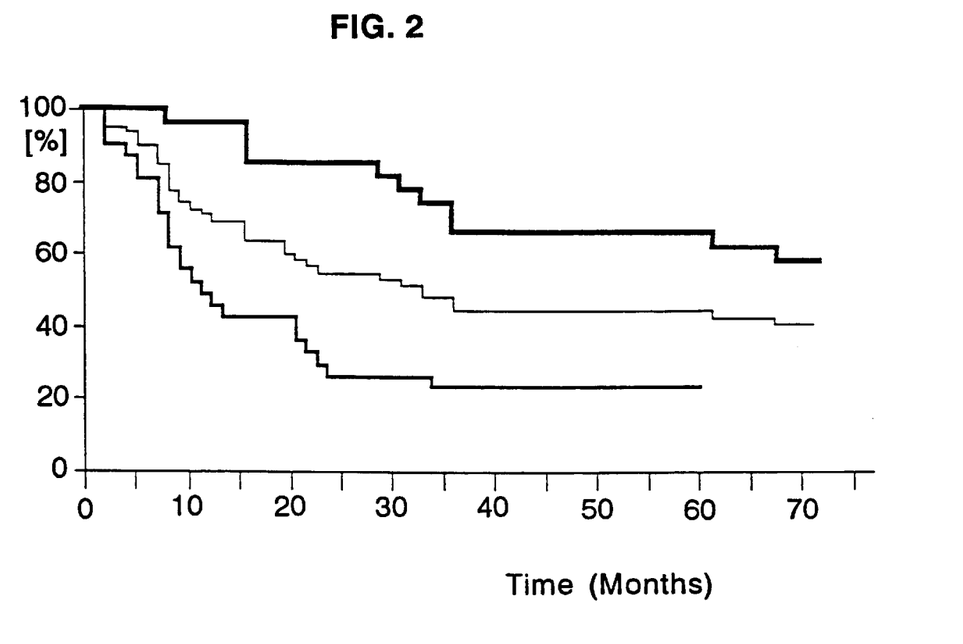
FIG. 2: The figure shows the survival rate of patients with epithelial ovarian carcinomas. The x-axis represents the survival time in months; the y-axis shows the percentage of living patients with advanced ovarian carcinoma. Group I (with the production of anti-idiotypic antibodies) (bold line) consists of 28 patients. Group II (without production of anti-idiotypic antibodies) (medium line) consists of 32 patients with a similar distribution of stages (FIGO III-IV), same operative and chemotherapeutical treatment, without immunotherapeutical therapy modalities. The thin line represents the total survival rate of the whole sample between 1985 and 1992. The difference between group I and II is highly significant ($p<0.001$, Wilcoxon).

The only side-effect which was detected, was an extreme increase of false positive values of the tumor marker concentration of CA125, measured by the Abbott CA125 EIA monoclonal (Abbott Diagnostic, Wiesbaden-Delkenheim, Germany), induced by the anti-idiotypic antibodies, Reinsberg et al., supra. Other side-effects, like anaphylactic reactions were not observed. Our first results of the inventors show that, even in advanced stages of the disease, the induction of an anti-idiotypic antibody (Ab2β) against OC125 mimicking the TAA class III CA125 leads to a prolongation of the survival rate. Compared to the survival rate of a group of patients that was related in the same manner, there was a striking difference for these patients, who had produced the anti-idiotype antibody; see FIG. 2, Wagner et al., supra. Thus, it is concluded that the anti-idiotypic antibodies of the present invention can advantageously be used as a vaccine in immunotherapy for the induction of an anti-tumoral immunity in patients suffering from CA125-positive carcinomas.

In a preferred embodiment of the present invention, the anti-idiotypic antibody has a binding constant to the monoclonal antibody OC125 of at least $2,3 \times 10^9 M^{-1}$ as determined according to the modified method of Wagner et al., J. Immunol. 130 (1983), 2302.

In another preferred embodiment, the anti-idiotypic antibody is a monoclonal antibody which is derived from any mammal, for example a rat, a mouse, a goat and the like by conventional techniques as described, for example, in Köhler and Milstein, Nature 256 (1975), 495, and Galfrè, Meth. Enzymol. 73 (1981), 3. Preferably, the anti-idiotypic antibody is derived from mice.

In a particularly preferred embodiment, the anti-idiotypic antibody of the invention is the antibody ACA125 which is produced by hybridoma 3D5, infra.

In a particularly preferred embodiment, the anti-idiotypic antibodies are recombinantly produced. Said antibodies can be prepared in accordance with conventional procedures. For example, the gene fragments coding for the variable regions of heavy and light chain of the anti-idiotypic antibody of the invention can be separated from other chromosomal genes contained, for example, in the antibody producing mouse hybridoma cells in accordance with usual procedures (cf. e.g., Maniatis et al., "Molecular Cloning", Cold Spring Harbor Lab. (1982) and Glover ed. "DNA Cloning Vol. I" IRL Press (1985)) by constructing a genomic library and screening for the genes encoding the variable regions of said antibody using, for example, a mouse IH probe.

After isolation of the relevant clones, the nucleotide sequences of the antibody V regions can be determined.

The DNA sequences which encode the variable regions of the heavy or light chain may be used to construct separate light and heavy chain gene transfection vectors which replicate and amplify in host cells as, for example, disclosed in Oi and Morrison, Biotechniques 4 (1986), 214 and EP-B1 0 194 276.

Another object of the present invention is to provide cell lines producing the monoclonal anti-idiotypic antibodies of the invention. Examples of such cell lines are 3D5 and 5A8, both producing monoclonal antibodies mimicking CA125.

In a preferred embodiment, said cell line is a hybridoma. The present invention particularly prefers hybridomas which are obtained by fusing BALB/c mice cells capable of producing the monoclonal antibody of the present invention with the myeloma cell line P3x63Ag8,653 which is described in detail in T. A. Springer (ed.): "Hybridoma Technology in the Biosciences and Medicine", Plenum Press, New York, 1985.

Particularly preferred is hybridoma 3D5 that produces ACA125. This hybridoma was deposited under the requirements of the Budapest Treaty on Mar. 22, 1993 at the DSM "Deutsche Sammlung von Mikroorganismen", 3300 Braunschweig, Mascheroder Weg 1B, Germany, under the accession number DSM ACC2120.

A further object of the present invention is to provide cell lines suitable for recombinant expression of the anti-idiotypic antibody. It would be clear to the person skilled in the art that a suitable host cell encompasses any cell, both eucaryotic or procaryotic, capable of effecting expression of the polypeptides encoded by the vectors mentioned above after transfection and, in addition, capable of allowing the proper formation of the recombinant antibody molecules within the host cell and the excretion of said antibody into the culture medium.

In another embodiment, the present invention relates to fragments of the anti-idiotypic antibody of the invention. These fragments typically have the binding specificity of said anti-idiotypic antibody of the invention. These fragments can be produced by conventional techniques as described in Boguslawski et al., J. Immunol. Meth. 120 (1989), 51, and Weir (Ed.), Handbook of Experimental Immunology, Blackwell, Edinburgh, 1986.

In a preferred embodiment, these fragments are f(ab)- or f(ab$_2$)-fragments.

A further object of the present invention is to provide pharmaceutical compositions comprising any of the anti-idiotypic antibodies of the invention or said fragments thereof in combination with a pharmaceutically acceptable carrier. These pharmaceutical compositions are suitable for the treatment of and vaccination against all CA125-positive malignant tumors, including ovarian carcinoma as the particularly preferred embodiment.

The preparation and formulation of such physiologically acceptable compositions with regard to pH, stability, etc. is within the skill of the art. Examples of suitable pharmaceutically acceptable carriers are well-known in the art and include phosphate buffered saline solutions, water, emulsions, such as oil/water emulsions, various types of wetting agents, sterile solutions, tablets, coated tablets, and capsules. Typically, such carriers contain excipients such as starch, milk, sugar, certain types of clay, gelatine, stearic acid or salts thereof, magnesium or calcium stearate, talc, vegetable fats or oils, gums, glycols, or other known excipients. Such carriers may also include flavor and color additives or other ingredients. Compositions comprising such carriers can be formulated by well-known conventional methods. These pharmaceutical compositions can be administered to the subject at a suitable dose. Suitable doses are in the range of 100 $\mu$g to 1 mg of the anti-idiotypic antibodies of the invention. Administration of the suitable compositions may be effected by different ways, e.g., by intravenous, intraperentoneal, subcutaneous, intramuscular, topical or intradermal administration.

Still a further object of the present invention is the use of said anti-idiotypic antibodies or fragments thereof as a standard for the calibration of a diagnostic kit for the determination of the presence or the concentration of CA125 in a sample used for the surveillance of CA125 concentration, e.g., in ovarian cancer patients. In the preferred embodiment, the sample is serum, plasma or effusion fluid.

A further object of the present invention is the use of said anti-idiotypic antibodies or fragments thereof as an antigen for the preparation of anti-CA125 antibodies. This production can be carried out by methods well-known in the art, for example, as described in Mitrahi (Ed.): Monoclonal Antibodies: Production and Application, Alan R. Liss, New York, 1989.

The present invention also provides a method for the production of the anti-idiotypic antibody, which comprises
(a) preparing an anti-CA-125 antibody;
(b) immunizing a mammal with the anti-CA125 antibody of step (a);
(c) fusing spleen cells of the immunized mammal with a myeloma cell line; and
(d) selecting a hybridoma producing said anti-idiotypic antibody.

Finally, the present invention provides a method for the recombinant production of an anti-idiotypic antibody. This method comprises the transfection of a suitable host cell with expression vectors encoding the polypeptides mentioned above, treating the transfected host cell so as to effect expression of the polypeptides encoded by said expression vectors and the proper formation of the recombinant antibody molecules within the host cell and excretion of said antibody into the culture medium, and recovering the excreted antibody molecules from the culture medium.

EXAMPLE 1

Production of Monoclonal Antibodies

Figure 3:
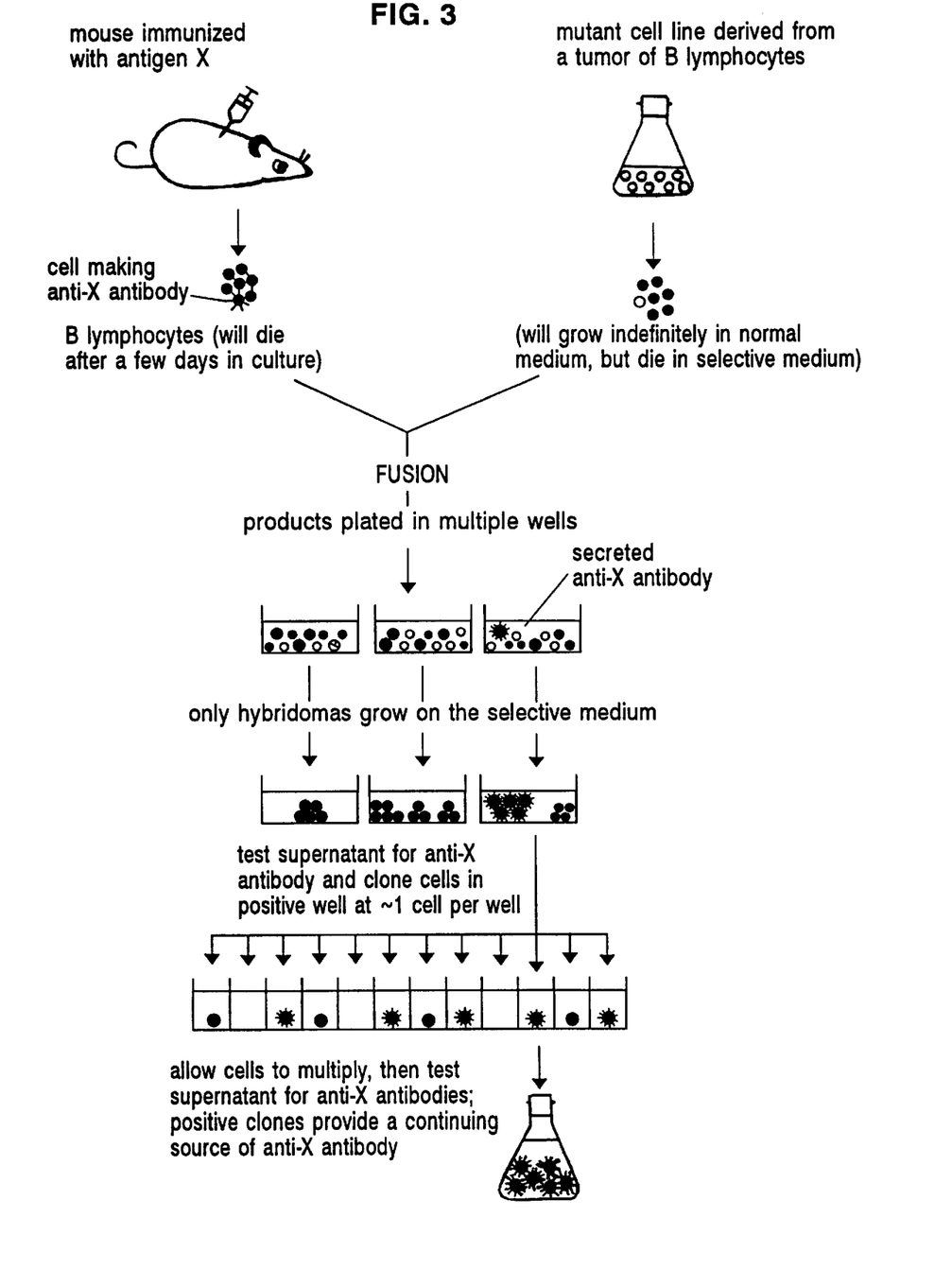
FIG. 3: Production of murine monoclonal antibodies.

Monoclonal antibodies producing hybridoma cells were developed by standard techniques; Galfrè and Milstein, supra, Köhler and Milstein, supra, Springer, ed., "Hybridoma Technology in the Biosciences and Medicine", Plenum Press, New York, 1985. The principle of the production of monoclonal antibodies by the induction of hybridoma cell is shown in FIG. 3.

EXAMPLE 2

Production of a Monoclonal Anti-Idiotypic Antibody

Female BALB/c mice (6 weeks old) were immunized with anti-CA125 antibodies taken from a commercial CA125 determination kit (Enzymun-Test CA125, Boehringer Mannheim, Mannheim, Germany) conjugated to Keyhole Limpet Hemocyanin (KLH) over a period of 3 months (first immunization: 100 µg, 3 times boost with 50 µg). Myeloma cell line P3x63Ag8,653 was used as the fusion partner. The resulting hybridoma cells were cultivated in RPMI 1640 medium with FCS and HECS.

Cells producing specific antibodies were subcloned for three times (limited dilution) according to standard methods. As a result, clone 3D5 was obtained.

EXAMPLE 3

Screening Assay for Anti-Idiotypic Antibodies

Microtiter plates were coated with F(ab)$_2$-fragments of the mAb OC125 antibody. Supernatants of hybridoma cell cultures were added and a POD-conjugated antibody (goat-anti-mouse IgG, Fc-fragment specific) was used for detection. The binding activity was determined according to the inhibition by the binding of the CA125 antigen.

For the determination of the binding affinity, the method described by Wagner et al, supra, was modified. Coster-RIA-strips were coated with 5 µg/ml wheat-germ-lectine and 2 µg/ml ACA125. A dilution series of the J-125-labeled antibody (0.02–10 µg/ml) was incubated for 4 hours under room temperature during constant shaking. Binding affinity was calculated from the ascent in the Scatchard-Plot (Wagner et al: "Quantification of Carcinoembryonic Antigen in Serum and Analysis of Epitope Specificities of Monoclonal Antibodies", Meth. Enzymol. 184 (1990), 507–518.

The hybridoma clone deposited as Clone 3D5 (DSM ACC2120) produces an IgG1K antibody (Ab2). The binding of this antibody to the mAbOC125 antibody (Ab1) is completely inhibited by the CA125 antigen:

| CA125 (U/Test) | Competition (%) |
|---|---|
| 50 | 7 |
| 150 | 23 |
| 500 | 33 |
| 800 | 51 |
| 1500 | 79 |
| 6000 | 90 |

The antibody IgG1K produced by hybridoma 3D5 (DSM ACC2120) has a binding constant to the antibody OC125 of at least $2,3 \times 10^9 M^{-1}$.

Furthermore, several clones producing an anti-anti-idiotypic antibody Ab3 (anti-CA125 antibody induced by immunization with an anti-CA125 antibody (OC125) via idiotypic cascades) against CA125 were detected during the subcloning procedure. This confirms our results that Ab2-producing cells were generated.

The monoclonal anti-idiotypic antibody mimicking the tumor-associated CA125 antigen produced by the hybridoma clone 3D5 named mAb "ACA125". F(Ab)2-fragments were purified according to standard techniques as described, e.g., in Goding: Monoclonal Antibodies: Principles and Practice, Academic Press London, 1986. The "Mouse Monoclonal Antibody Isotyping Kit" (Amersham International PLC, Amersham, U.K.) was used for isotype determination. The antibody was found to be IgG1 K.

This antibody (ACA125) can be used as a vaccine for the induction of an anti-tumor immunity in patients with CA125-positive carcinomas.

Figure 1:
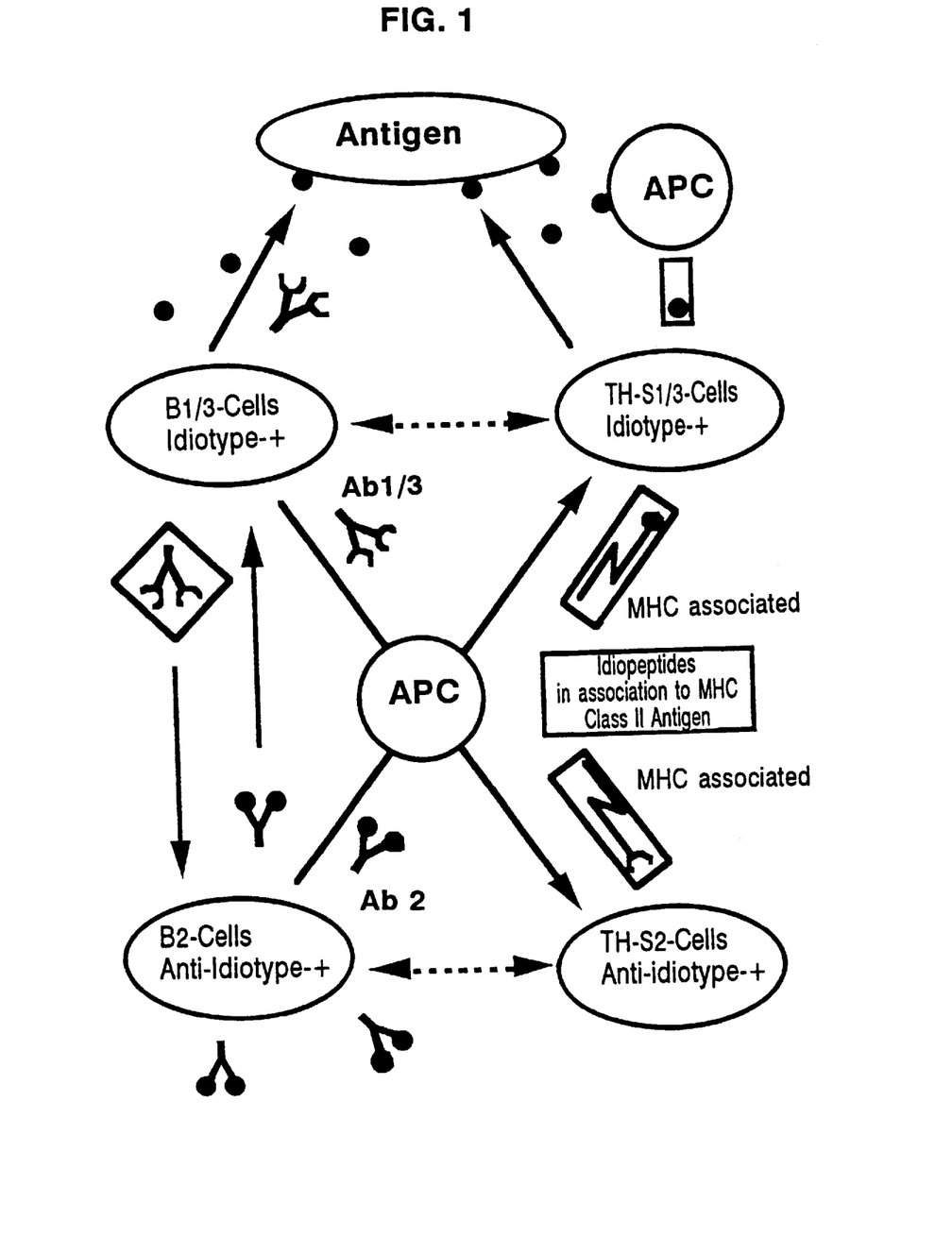
FIG. 1: Idiotypic and anti-idiotypic responses initiated by the application of monoclonal antibodies (Ab1) against a tumor-associated antigen. The Ab1 leads to an induction of idiotype positive B-cells producing anti-idiotypic antibodies (Ab2) in the patient. These Ab2s may subsequently react in two ways: first, they induce the production of Ab3s, which then are again directed against the tumor-associated antigen, or, second, they can lead to a new antigen presentation and, thus, to a modulation of the immune response by the induction of idiotype positive T-cells; Cerny and Hiernaux, supra.

This anti-idiotypic CA125 imitating murine monoclonal antibody (ACA125) is a transformation of the epitope CA125 into an idiotypic determinant; see FIG. 1. ACA125 induces a T-cell specific anti-tumoral immunity against CA125-positive malignant tumors. On the other hand, ACA125 also leads to the induction of anti-anti-idiotypic antibodies (Ab3), which can bind to a CA125-positive tumor tissue and can induce an antibody-dependent cell-mediated cytotoxicity.

EXAMPLE 4

In Vivo Experiments (I) In vivo Experiments with mAb ACA125

Figure 4:
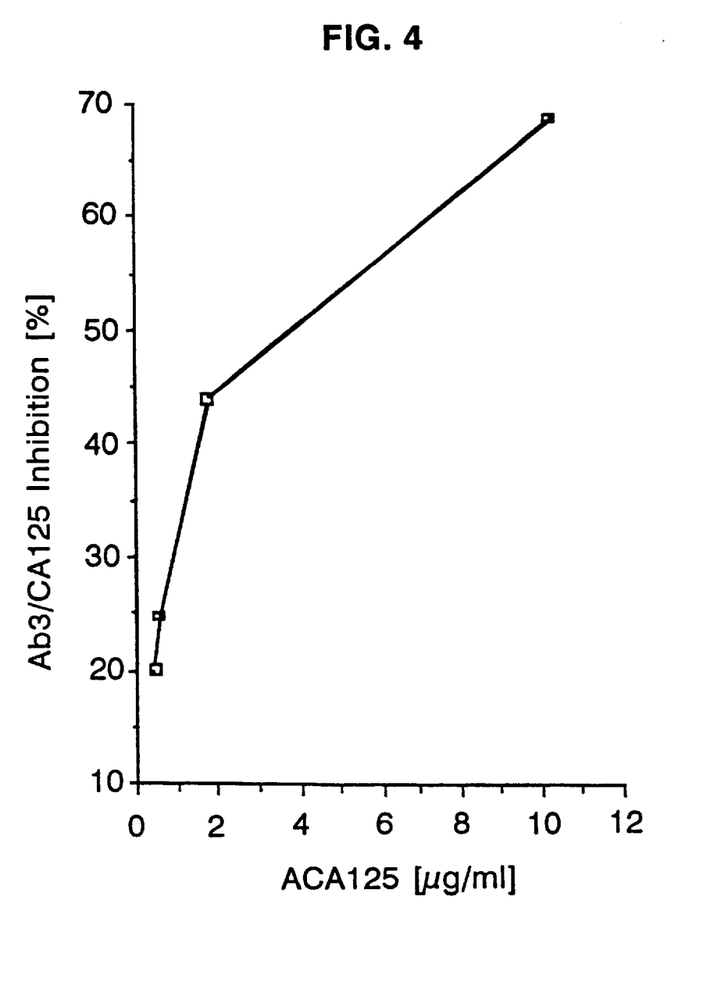
FIG. 4: The figure shows the inhibition of the binding of anti-CA125 antibodies (Ab3) in rats after immunization with the anti-idiotypic mAb ACA125 in competition with CA125 antigen.

The in vivo experiments with mAb ACA125 showed that it is able to induce an anti-anti-idiotypic response in form of anti-CA125 antibodies in rats (IgM/IgG) (FIG. 4).

Figure 5:
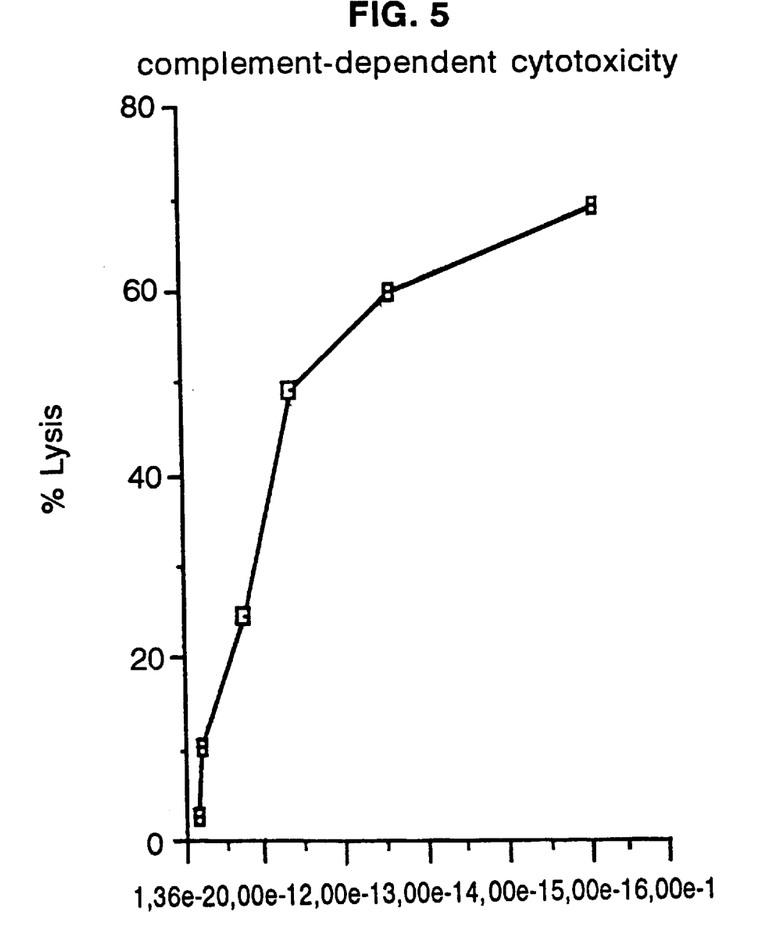
FIG. 5: The figure shows the complement dependent lysis of CA125-positive target cells by the induced Ab3.
Figure 6:
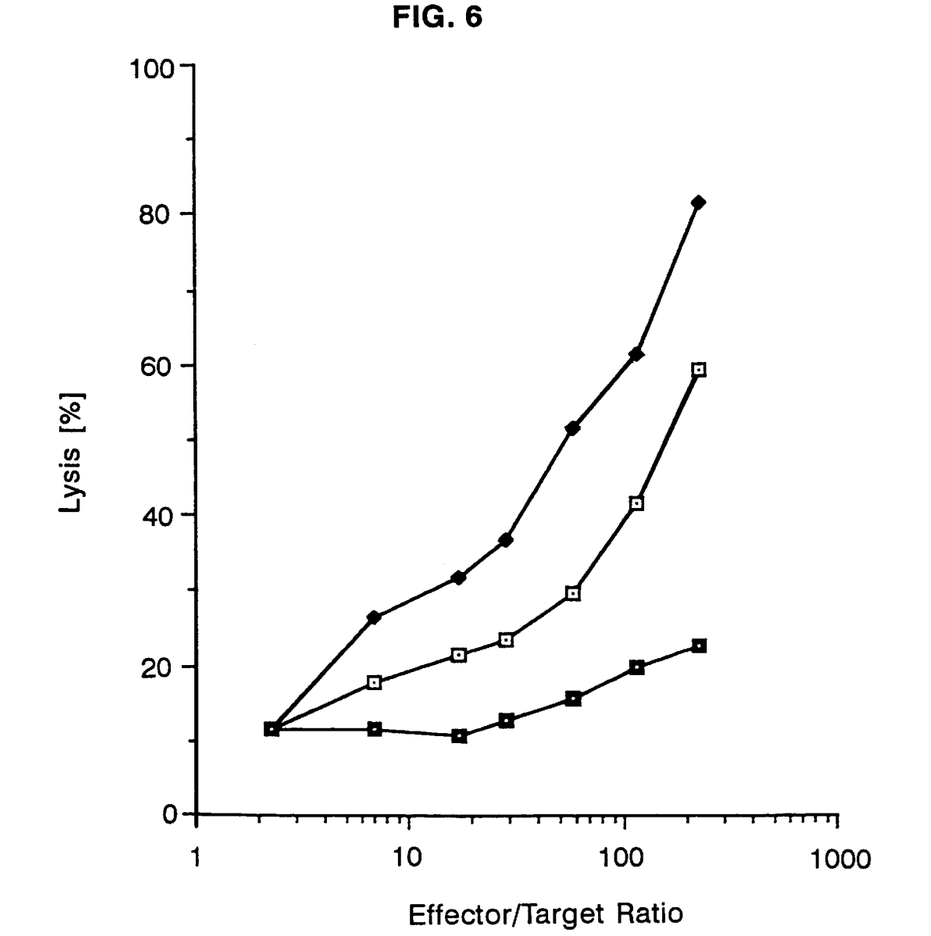
FIG. 6: Antibody-dependent cell-mediated cytotoxicity -ADCC- after immunization with Ab2 in rats.
Figure 7A:
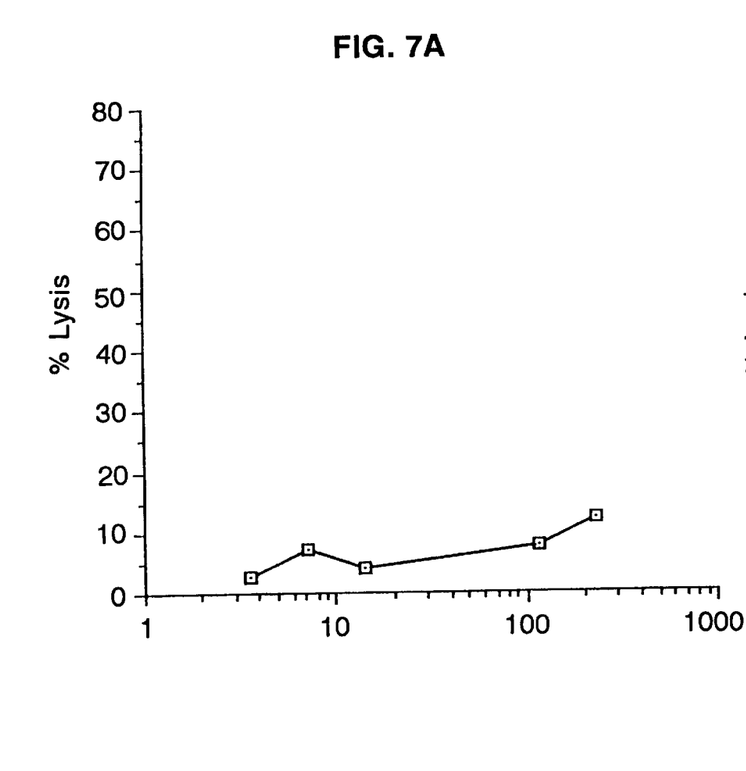
FIG. 7: Cell-mediated lysis of effector cells from non-immunized animals (left) and animals after the application of F(ab')2-fragments of the mAb ACA125. The superior graph shows the lysis from the CA125-non-expressing SK-OV3 cell line and the inferior graph for the CA125-expressing NIH-OVCAR3, which shows a maximum lysis of about 60%.
Figure 7B:
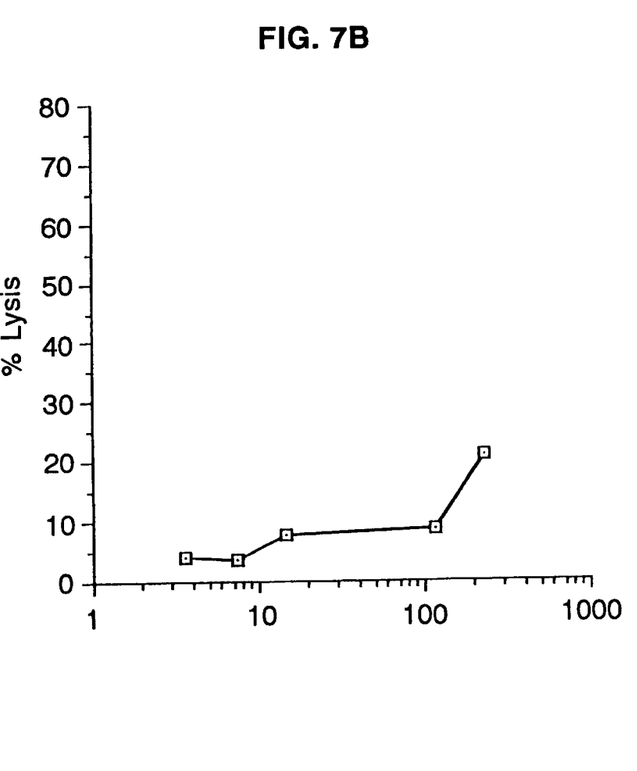
Figure 7C:
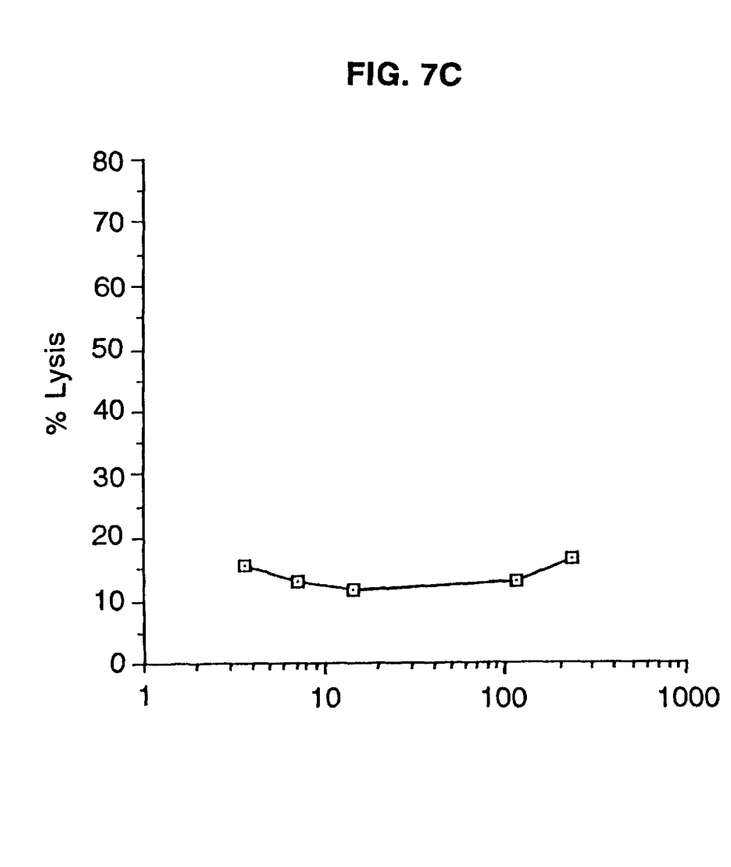
Figure 7D:
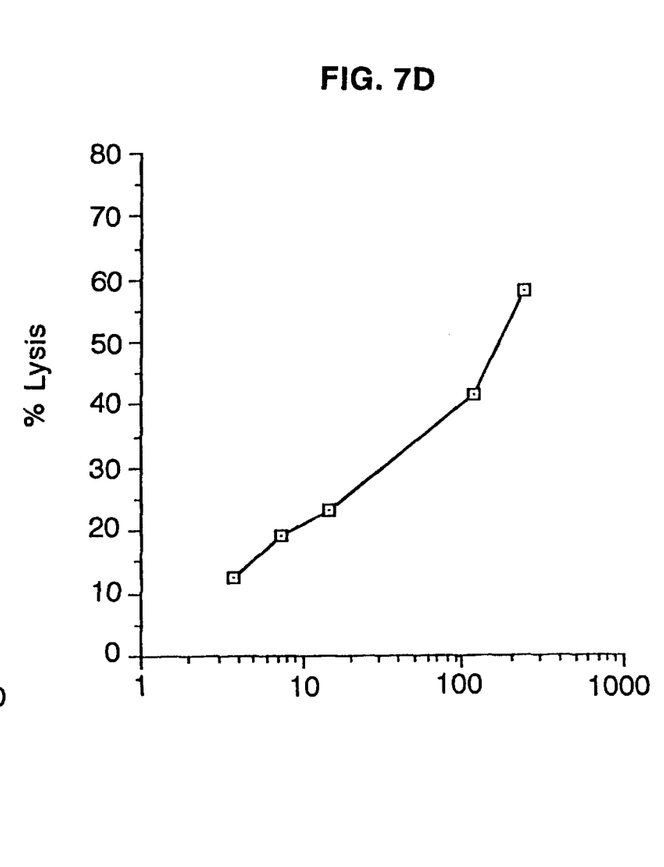

These so-called Ab3 are able to induce a complement cytotoxicity -CDC- (FIG. 5) as well as an antibody-dependent cell-mediated cytotoxicity -ADCC- (FIG. 6).

Furthermore, it could be demonstrated that by repeated immunization with mAb ACA125 mimicking the tumor-associated antigen CA125, a cell-mediated cytotoxicity, which is specific for CA125-expressing cell lines, could be induced (FIG. 7).

In summary, this monoclonal anti-idiotypic antibody mimicking the tumor-associated antigen CA125 (mAb ACA125) showed to be able to induce a CDC, ADCC and a cell-mediated cytotoxicity for CA125-expressing cell lines. So this anti-idiotypic antibody fulfils the recent immunological criteria (Steplewski: Advances and Outlooks for Immunotherapy of Cancer, Hybridoma, 12 (1993), 493–500) for monoclonal antibody immunotherapy using the anti-idiotypic network approach.

(II) In vivo Experiments with F(ab')2-fragments

For in vivo experiments, F(ab')2-fragments were prepared according to published standard techniques (Goding: Monoclonal Antibodies: Principles and Practice, Acad. Press London 1986). For the induction of anti-anti-idiotypic responses, rats (n=3) were immunized with F(ab')2-fragments of mAb ACA125. After immunization with 100 µg of F(ab')2 ACA125 (3 times boostering), an anti-anti-idiotypic answer arose (IgM/IgG). The specific binding activity of the so-called Ab3 could be inhibited by the anti-CA125 antibody used for the induction of ACA125 (FIG. 4). Unimmunized rats were used as control.

(III) CDC

For the determination of the complement-mediated cytotoxicity, the sera of immunized (after application of F(ab')2 mAb ACA125) and unimmunized rats were detected for the complement-dependent lysis of 111-Indium-labeled NIH-OVCAR3 CA125-expressing tumor cell line as a target according to standard techniques (Goding: Monoclonal Antibodies: Principles and Practice, Acad. Press London 1986). FIG. 5 shows complement-dependent lysis of anti-CA125 antibodies induced by the immunization with F(ab')2 mAb ACA125 determined by counts of released radioactivity.

(IV) ADCC

For the determination of the antibody-dependent cellular-mediated cytotoxicity, peripheral mononuclear blood cells (PMBC) and thymus-originated T-cells were purified and concentrated by FICOLL gradient and used as effector cells. A commercial CA125-expressing tumor cell line (NIH-OVCAR3) was used as a target. Effector and target cells were incubated according to standard techniques and sera of immunized and unimmunized animals were added in a serial dilution (Krueger: Klinische Immunpathologie, Kohlhammer, Stuttgart 1985). Released radioactivity correlates with the antibody-cell-mediated lysis (FIG. 6).

(V) Cell-mediated Cytotoxicity

For the determination of the cellular-mediated cytotoxicity, peripheral mononuclear blood cells (PMBC) and thymus-originated T-cells were purified and concentrated by FICOLL gradients and used as effector cells. As target cells, a commercial CA125-non-expressing (SK-OV3) and a highly CA125-expressing cell line (NIH-OVCAR3) were used. Radioactive labeled target cells and lymphocyte-suspensions in raising cell concentrations were incubated according to standard techniques to determine cell-mediated lysis (Krueger, supra). FIG. 7 shows the released radioactivity determined as the percentage of cell lysis of non-immunized controls on the left side and the immunized animals on the right side. The superior graph shows the lysis with the non-expressing SK-OV3 cell line and the inferior graph for the CA125-expressing NIH-OVCAR3.

What is claimed is:

1. An anti-idiotypic antibody which is the monoclonal antibody ACA125 produced by hybridoma 3D5 (DSM ACC2120).

2. The anti-idiotypic antibody according to claim 1, which is recombinantly produced.

3. A fragment of an anti-idiotypic antibody according to claim 1, which has the binding specificity of said anti-idiotypic antibody.

4. The fragment according to claim 3, which is an f(ab) or f(ab)$_2$-fragment of said anti-idiotypic antibody.

5. A cell line producing the monoclonal antibody according to claim 1.

6. The cell line according to claim 5, which is a hybridoma.

7. The cell line according to claim 6, which is hybridoma 3D5 (DSM ACC2120).

8. A pharmaceutical composition comprising an anti-idiotypic antibody according to claim 1 and a pharmaceutically acceptable carrier.

9. The pharmaceutical composition according to claim 8 for the treatment of CA125-positive malignant tumors.

10. The pharmaceutical composition ion according to claim 9, wherein the malignant tumor is epithelial ovarial cancer.

11. A method of treatment of CA125-positive tumors which comprises administering to a subject a pharmaceutical composition comprising an anti-idiotypic antibody according to claim 1.

12. The method according to claim 11, wherein the CA125-positive tumor is epithelial ovarial cancer.

13. A kit for determination of CA125 in a sample comprising an anti-idiotypic antibody according to claim 1 as a standard for calibration.

14. The kit according to claim 13, wherein the sample is serum, plasma or effusion fluid.

15. A method for the production of anti-CA125 antibodies which comprises, immunizing with an anti-idiotypic antibody according to claim 1 as an antigen and thereby obtaining the anti-CA125 antibodies.

16. A method for the production of an anti-idiotypic antibody according to claim 1, comprising culturing the hybridoma 3D5 (DSM ACC2120) and obtaining the antibody from the culture medium.

17. Method for the recombinant production of an anti-idiotypic antibody according to claim 2, which comprises:
   (a) transfecting a host cell with expression vectors encoding at least the variable regions of the light and heavy chain of said antibody;
   (b) treating the transfected host cell so as to effect expression of the polypeptides encoded by said expression vectors and proper formation of the recombinant antibody molecules; and
   (c) recovering the secreted antibody molecules from the culture medium.

18. A pharmaceutical composition comprising a fragment according to claim 3 and a pharmaceutically acceptable carrier.

19. The pharmaceutical composition according to claim 18 for the treatment of CA125-positive malignant tumors.

20. The pharmaceutical composition according to claim 19, wherein the malignant tumor is epithelial ovarial cancer.

21. A method of treatment of CA125-positive tumors which comprises administering to a subject a pharmaceutical composition comprising a fragment according to claim 3.

22. The method of claim 21, wherein the CA125-positive tumor is epithelial ovarial cancer.

23. A kit for determination of CA125 in a sample comprising a fragment according to claim 3 as a standard for calibration.

24. The kit according to claim 23, wherein the sample is serum, plasma or effusion fluid.

25. A method for the production of anti-CA125 antibodies which comprises immunizing with a fragment according to claim 3 as an antigen and thereby obtaining the anti-CA125 antibodies.

26. The monoclonal antibody according to claim 1, having the following features:
   (a) it reacts with an anti-CA125 antibody,
   (b) it competes with CA125 in its binding to said anti-CA125 antibody,
   (c) it leads to the induction of anti-anti-idiotypic antibodies (Ab3), and
   (d) it induces an antibody-dependent cell-mediated cytotoxicity (ADCC) and a cell-mediated cytotoxicity.

27. The anti-idiotypic antibody according to claim 26, which has the following additional feature:
   (e) a binding constant to the monoclonal antibody OC125 of at least $2,3 \times 10^9 M^{-1}$.

* * * * *